US005472444A

United States Patent [19]
Huebner et al.

[11] Patent Number: 5,472,444
[45] Date of Patent: Dec. 5, 1995

[54] HUMERAL NAIL FOR FIXATION OF PROXIMAL HUMERAL FRACTURES

[75] Inventors: Randall J. Huebner; Gene L. Conrad, both of Aloha, Oreg.

[73] Assignee: Acumed, Inc., Beaverton, Oreg.

[21] Appl. No.: 242,738

[22] Filed: May 13, 1994

[51] Int. Cl.⁶ .................................................. A61B 17/72
[52] U.S. Cl. ................................................ 606/64; 606/62
[58] Field of Search ................................. 606/62, 63, 64, 606/67, 68, 65, 66, 60, 72, 73, 80, 84, 85, 96, 98, 99, 100, 104, 105; 623/16, 18, 19

[56] References Cited

U.S. PATENT DOCUMENTS

| 4,135,507 | 1/1979 | Harris | 606/62 X |
| 4,475,545 | 10/1984 | Ender | 606/64 X |
| 4,503,847 | 3/1985 | Mouradian | 606/64 X |
| 4,522,202 | 6/1985 | Otte et al. | 606/62 X |
| 5,035,697 | 7/1991 | Frigg | 606/67 |
| 5,066,296 | 11/1991 | Chapman et al. | 606/64 |
| 5,248,313 | 9/1993 | Greene et al. | 606/62 |

FOREIGN PATENT DOCUMENTS

| 355411 | 2/1990 | European Pat. Off. | 606/62 |

OTHER PUBLICATIONS

Gamma Locking Nail system, et seq, Howmedica Product Catalog, section J, pp. 2–5, 16–19, 21–27, date and author unknown.
Uniflex Humeral Nail System, Biomet Product Brochure, date and author unknown.
Uniflexibility, The Uniflex Nailing System, Biomet Product Brochure, date and author unknown.
Stainless Steel Taper Small Bone Locking Nail, Biomet Product Brochure, date and author unknown.
The Intermedics Select Shoulder System, Intermedics Product Brochure, Jul. 1990, author unknown.
The Intermedics Select Shoulder System, Surgical Technique, Wayne Z. Burkhead, Jr., Md., date unknown.
True/Flex Torsionally Resistant Upper Extremity/Flexible, Applied Osteo Systems, Inc. Product Brochure, date and author unknown.
Surgical Technique—AIM Titanium Femoral Nail System, Ace Product Brochure, date unknown, author unknown.
Surgical Technique—AIM Titanium Tibial Nail System For Unreamed and Reamed Indications, Ace Product Brochure, date unknown, author unknown.
Nail Challenges Plate, Screw for Tough Femur Fractures, Orthopedics Today, vol. 13, No. 9, pp. 1, 20–21, Sep. 1993, author unknown.
Four–Part Valgus Impacted Fractures of the Proximal Humerus, Jakob, et al., J Bone Joint Surg (Br) 1991; 73-B:295-8.
Manual of Internal Fixation Techniques Recommended by the AO Group, 2nd ed., M. E. Müller, 1979 Section 1.3, Fractures of the Humerus, pp. 168, 169, 172, 173.

Primary Examiner—Stephen C. Pellegrino
Assistant Examiner—Guy V. Tucker
Attorney, Agent, or Firm—Bennet K. Langlotz

[57] ABSTRACT

An elongated tapered nail or rod having an elongated body with a curved tapered shank that may be secured within a proximal portion of the humeral shaft, with a contiguous butt portion of the nail extending proximally from the shank to provide a solid foundation to which the humeral head fragments may be secured. The butt portion has transverse holes oriented at selected angles to receive fasteners attached to the fragments. The nail has a varying taper angle that creates a ridge positioned away from the distal tip, reducing stress concentrations on the bone that may occur at the tip of any reinforcing implant.

22 Claims, 3 Drawing Sheets

HUMERAL NAIL FOR FIXATION OF PROXIMAL HUMERAL FRACTURES

FIELD OF THE INVENTION

This invention relates to apparatus for treatment of bone fractures, and more particularly to apparatus for fixation of fractures of the proximal humeral cortex.

BACKGROUND AND SUMMARY OF THE INVENTION

The humerus bone of the upper arm is part of a "ball and socket" joint at the shoulder. The proximal end of the humerus has an enlarged head or cortex that includes the "ball." The humeral shaft extends distally away from the proximal head toward the elbow joint.

Proximal humeral fractures are the most common humeral fractures. These are often found in patients who have fallen on their arms, creating an axial load on the humerus that causes a fracture of the humeral head. In a two-part fracture, The head or a single portion of the head is broken from the humeral shaft. Three- and four-part fractures involve the fracture of the humeral head into two or three fragments separate from the shaft. The nature of these fractures is generally predictable, as the head tends to fracture between the ball portion and one or both tubercles of the head to which ligaments attach. Proximal humeral fractures are particularly problematic in elderly, osteoporotic patients, and in those patients having cancerous tissue in the region of the fracture.

Existing treatments for multiple proximal humeral fractures may be unsatisfactory in many cases. Conventional techniques for wiring, suturing, or externally fixing fragments to each other and to the shaft are not entirely suitable for treatment of more complex fractures, or when tissues are weakened by disease. In these cases, surgical replacement of the shoulder joint may be required.

To avoid the more drastic measure of joint replacement, the present invention provides an elongated tapered nail or rod having an elongated body with a curved tapered shank that may be secured within a proximal portion of the humeral shaft, with a contiguous butt portion of the nail extending proximally from the shank to provide a solid foundation to which the humeral head fragments may be secured. The butt portion has transverse holes oriented at selected angles to receive fasteners attached to the fragments.

The curved tapered shape of the present invention permits it to be inserted into a cavity formed by a broach tool having the same shape as the nail, without significant interference or flexing of the bone or nail during insertion, and without broaching a too-large cavity having excessive clearance that would permit a loose fit between nail and bone. Also, the nail has a varying taper angle that creates a ridge positioned away from the distal tip, reducing stress concentrations on the bone that may occur at the tip of any reinforcing implant.

DETAILED DESCRIPTION OF A PREFERRED EMBODIMENT

Figure 1:
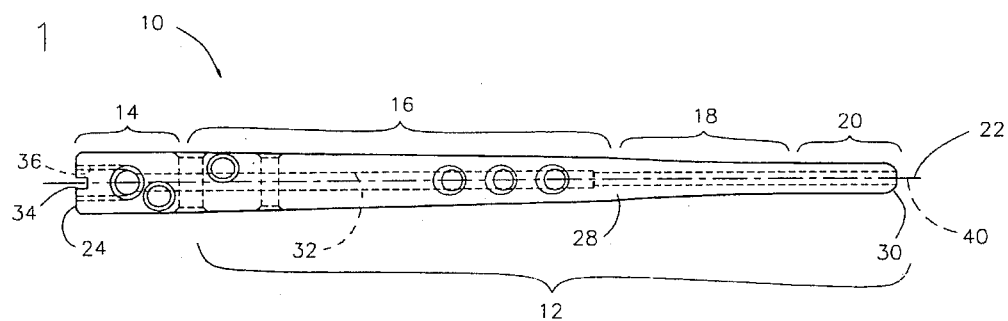
FIG. 1 is a side view of a preferred embodiment of the invention.

FIG. 1 shows a humeral rod or nail 10. The nail includes a tapered shank 12 and a cylindrical butt 14. The shank includes a curved, conically tapered first section 16 contiguous with the butt, a concavely tapered extending portion 18 extending distally from the first portion 16, and a cylindrical distal portion 20 extending distally from the extending portion. The various portions of the nail have various taper angles, while these portions have matched diameters at their junctions to create a continuous, step-free surface. The nail has a varying circular cross section throughout its length, centered on an axis 22 that has straight portions and curved portions, as will be discussed below with respect to FIG. 2.

The butt portion 14 has a chamfered end 24 forming the proximal end of the nail 10. In the preferred embodiment of the invention, the butt portion 14 is 0.598 inch long, 0.4375 inch in diameter, and has no taper. The first tapered section 16 has a length of 3.10 inches, tapers from the butt diameter to a distal diameter of 0.312 inch, with a straight taper angle of 1.12 degrees. The concavely tapered extending portion 18 joins the first section 16 at a crest or ridge 28. The extending portion 18 has a length of 1.43 inches, and tapers from 0.312 inch to 0.218 inch. It has a toroidal, negatively curved surface defined as a surface of revolution of a circle having a radius of 21.06 inches centered 21.71 inches perpendicularly away from a point on the axis 22 at the distal end of the extending portion. The extending portion's taper angle diminishes from 3.89 degrees to 0 degrees. Consequently, the crest 28 forms a "bulge" with a transition angle of 2.77 degrees between the first portion 16 and the extending portion 18. The distal portion 20 is a straight cylinder 0.71 inch long, 0.218 inch diameter, with a hemispherical distal end 30 forming the distal tip or nose of the nail.

The nail 10 is cannulated to permit it to be inserted over a pre-inserted wire whose position has been radiographically confirmed prior to broaching a bone cavity and inserting the nail. The nail 10 has an axial bore 32 having a diameter of 0.125 inch within the butt 14 and first section 16, and having a narrowed diameter of 0.093 inch within sections 18 and 20. A notch or alignment element 34 at the butt end provides a positioning reference to enable a surgeon to determine the position of nail features concealed after implanting. A threaded pocket 36 is defined in the proximal end 24 to provide attachment to insertion tools and alignment jigs for surgery.

Figure 2:
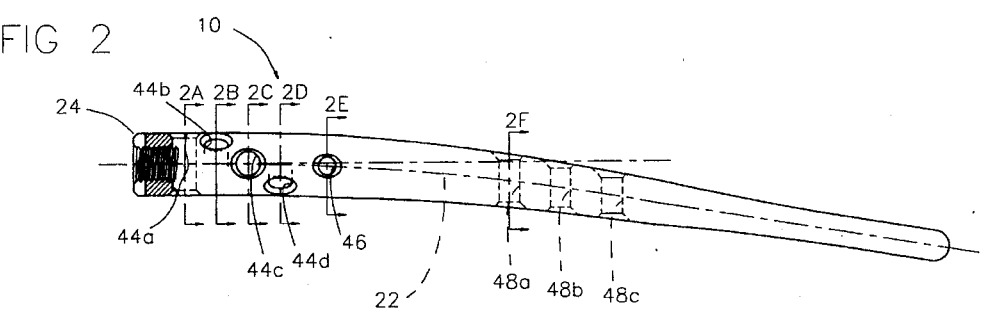
FIG. 2 is a side view of the embodiment of FIG. 1.
Figure 2A:
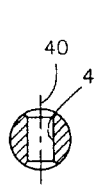
FIGS. 2A–2F are axial cross sectional views taken along the indicated lines in FIG. 2.

FIG. 2 shows a side view 10 illustrating the curved axis 22 of the nail. The axis is straight within portions 14, 18 and 20, and forms a 6.92 degree arc within the first tapered section 16. The axis occupies a reference plane 40 shown in FIG. 1. The reference plane occupies the page in FIG. 2.

FIG. 2 further illustrates a plurality of transverse holes, each of which is defined on a respective axis intersecting the nail axis 22, and perpendicular to the portion of the nail axis at the butt portion 14 of the nail. Each transverse hole is oriented at a selected angle with respect to the reference plane. Proceeding from the proximal end to the distal end of the nail, there are three sets of transverse holes: proximal holes 44a–44d, intermediate hole 46, and distal holes 48a–48c. The proximal holes are for securing humeral head fragments to the pin; the intermediate and distal holes are for securing the pin to the humeral shaft, as will be discussed below.

Figure 2B:
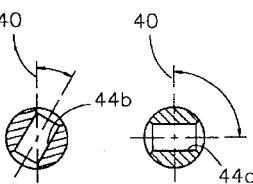
Figure 2C:
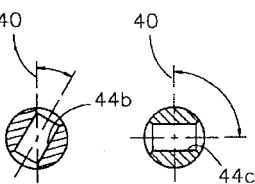
Figure 2D:
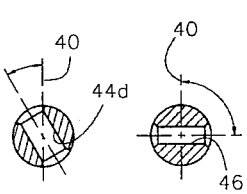
Figure 2E:
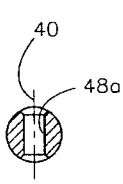
Figure 2F:
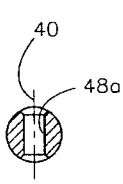

Again proceeding from butt to tip, transverse hole 44a is oriented with its axis within the reference plane 40 and perpendicular to the nail axis 22; hole 44b is offset 30 degrees clockwise from the reference plane when viewed from the butt end as shown in FIG. 2B, hole 44c is perpendicular to the reference plane; and hole 44d is offset 30 degrees counter-clockwise from the reference plane when viewed from the butt end as shown in FIG. 2D. The intermediate hole 46 is oriented perpendicular to the reference plane, and the distal holes are oriented within the reference plane and perpendicular to the butt end portion of the nail axis 22. Each transverse hole passes entirely through the nail, and is chamfered where it enters and exits the nail. The nail may be constructed so that at least one of the transverse holes in the butt portion is offset from the reference plane by less than 45 degrees. The nail may define a distal transverse hole and may comprise a tip portion extending distally beyond the distal hole by a distance 20–50% of the total length of the nail.

Figure 3:
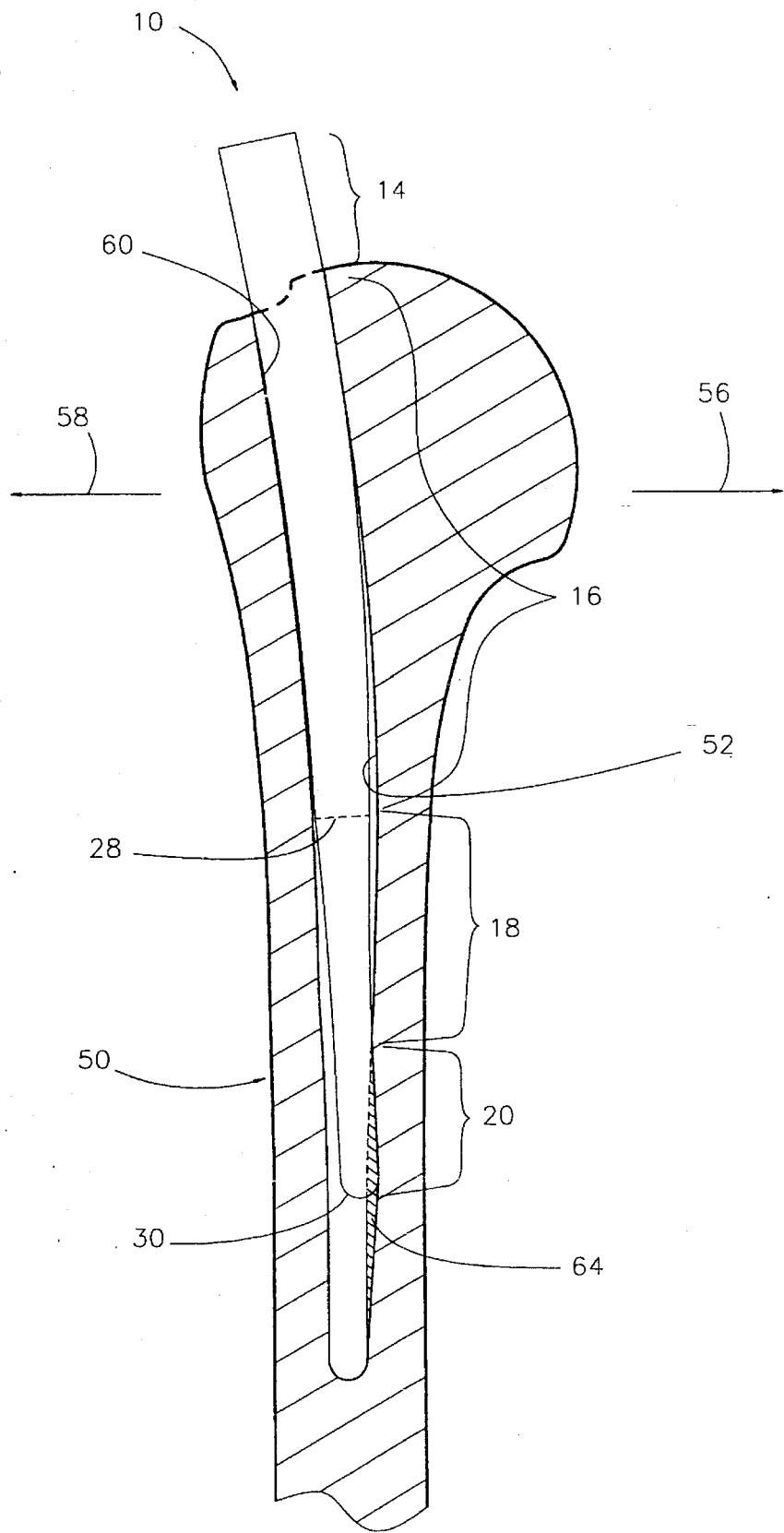
FIG. 3 is a side view illustrating a partially inserted nail according the embodiment of FIG. 1.

FIG. 3 shows the nail 10 partially inserted into a humeral shaft 50. The shaft defines a broached bore 52 having substantially the same shape as the shank of the nail. Although the bore is illustrated as being defined in a uniform solid material, the bone is actually hollow through the center of the shaft. Thus, the broaching process does not necessarily disrupt hard or solid tissue at the deepest portions of the bore.

A broaching tool is essentially a rasp having the same profile as the hole it is intended to form. In this instance, the broach would have the same shape as the nail 10. A broach is axially forced into and out of material without rotation to form a precisely shaped hole. A broach generally causes less tissue damage than a rotating drill bit or reamer. Broaches are also more effective at the difficult task of shaping bone fragments to provide a suitable bore when the fragments are assembled; a spinning reamer risks excess tissue damage.

Broaching is only suitable for certain shapes of holes and objects. Because the nail 10 is gently curved over a significant fraction of its length, it is said to largely "pass through its own envelope." An object with this property may enter a conforming space that leaves no gaps after installation, and which does not require distortion or flexing of the object or of the medium defining the space. A straight cylinder and a curved, tapered tusk-like element are examples of objects that have this property. Objects with angled bends or small radius curves (relative to the object length) do not pass through their own envelope on insertion, and are not well suited to insertion into a broached hole. The advantages of insertion are also realized if it is necessary to remove an implant without risking fracture of a healed bone.

The preferred embodiment of the invention does not perfectly pass through its own envelope, but departs very slightly from such a profile while avoiding tissue disruption significantly in excess of that required to form the bore 52. This departure can be quantified as an occupation area efficiency equal to the cross sectional area of the inserted object divided by the area of the hole, with the areas being taken in the reference plane 40. Because the distal portion 20 of the nail 10 is straight, the nail shank has an occupation area efficiency slightly less than 1.0, but has strength and functionality advantages that more than offset the slight reduction in area efficiency. An area efficiency greater than 0.85 provides acceptable results without unacceptable tissue disruption or weakening, and without significantly diminishing the surface contact between the nail and bone that provides a secure bond. In the illustrated embodiment, the rod has an area of 2.031 square inches, the envelope or bore 52 has an area of 2.097 square inches, resulting in an area efficiency of 97%.

FIG. 3 is labeled to indicate the medial direction 56 and the lateral direction 58 with respect to the patient's anatomy. The nail 10 is shown in a position in which the distal end 30 departs most widely from the ideal path. With the shaft aperture 60 essentially occupied by the nail, and the nail crest 28 pressing against the lateral side of the shaft bore 52, the tip 30 is forced to follow a groove 64. This groove 64 has been provided by broaching the bore, and is not occupied by the nail it its fully inserted position. As noted above, the hollow nature of the bone may mean that the groove is defined through fluid or soft bone tissue. Insertion is readily achieved without significantly flexing the bone shaft. Because the cylindrical butt portion 14 is typically received within broken humeral head fragments, its shape does not normally affect insertion efficiency concerns.

Figure 4:
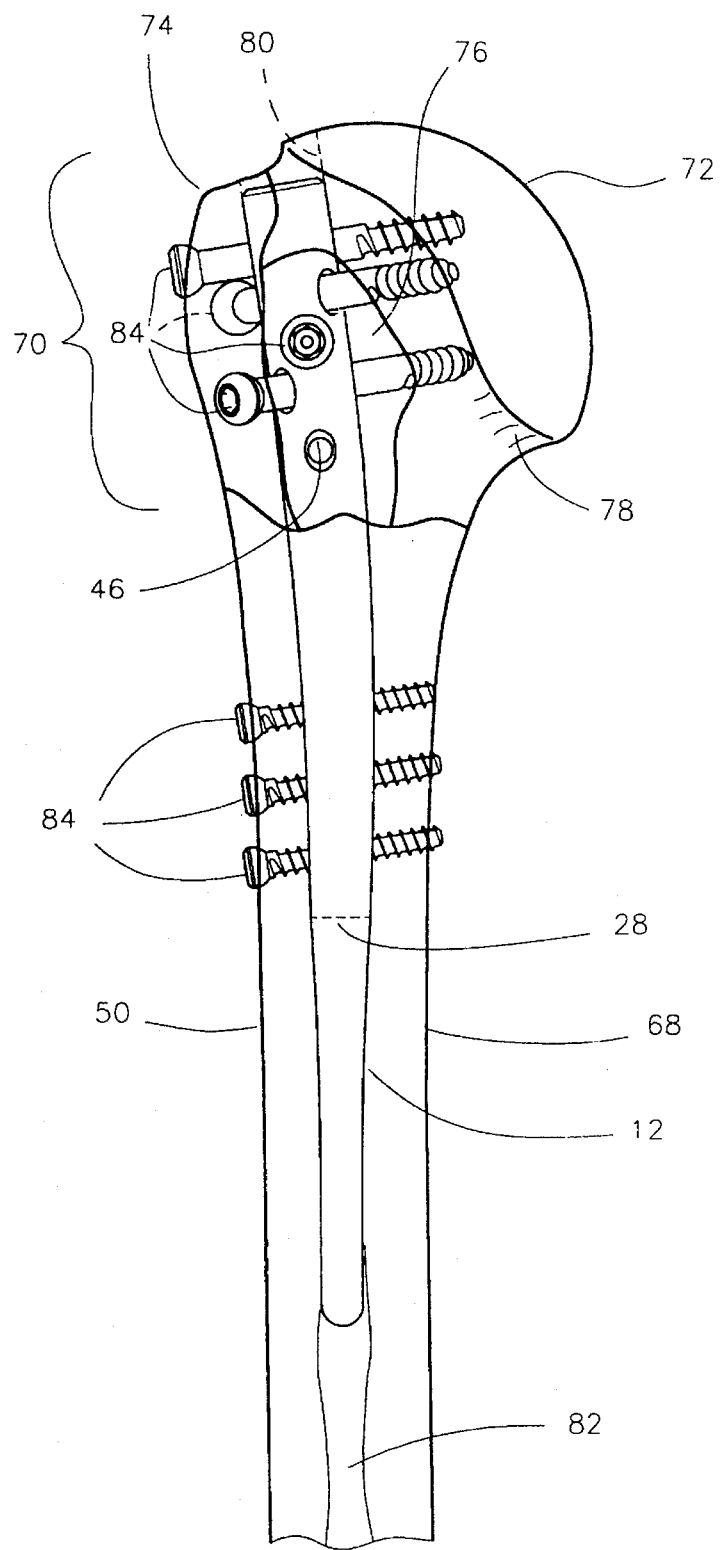
FIG. 4 is a side view illustrating the embodiment of FIG. 1 as implanted.

FIG. 4 illustrates the humeral nail 10 as fully implanted in an anterior view of the right humerus 68. The humeral head or cortex 70 includes the "ball" or articular surface 72, and the greater and less tubercles 74, 76. An anatomical neck 78 girdles the ball. The curve of the nail 10 permits its insertion through an aperture 80 between the ball and the greater tubercle at the top of the humerus, while permitting the shank 12 of the nail to follow the shape of the bone shaft 50. It is advantageous to avoid interfering with the articular surface, as that may diminish the patient's range of arm motion after treatment.

To reduce stress concentrations that can cause post-operative fracture, the tip 30 is positioned well away from the most distal hole 48c. To further reduce stress at the tip, the ridge or crest 28 provides a slightly increased resistance to bone flexing of small amounts. The crest "absorbs" a tolerable level of stress, which essentially distributes that portion of the stress away from the tip. This increases the force the bone can withstand. The distance between the crest 28 and hole 48c is about 0.25 inch in the illustrated embodiment, and should be at least 3–10% of the rod length, or between about 1–2 times the rod diameter at the crest.

The humeral shaft naturally includes a central portion filled with softer bone material. A narrowing of this central portion occurs at a diaphysis 82, which is at approximately the midpoint of the humerus, or about six inches from either end. The preferred six-inch length of the nail is selected to avoid interference with the diaphyis, although a longer nail may be employed with the narrowest nose portion passing throughout the diaphysis. In patients with differently sized bones, longer or shorter nails may be used. In general, it is preferred that the entire nail, or at least the wider portions thereof, be limited to less than or equal to half the length of an adult humerus, which is typically about twelve inches.

FIG. 4 shows a plurality of bone screws 84 installed to secure the nail 10 to the bone shaft 50, and to secure portions of the head 70 to the nail. The head will have typically been fractured into one or more fragments, often separating the ball from the other head portions, and from the shaft. Each screw has an outside thread diameter smaller than the diameter of the transverse hole that receives it, with each end of each screw engaging bone on opposite sides of the nail. The screws within holes 46a–46c and 48a–48c prevent rotation or axial movement of the nail, and engage opposite sides of the typically unbroken shaft 50. The screws securing the head portion through holes 44a–44d secure head fragments on opposite sides of the nail. The predictability of fracture modes makes the orientation of holes in the illustrated embodiment suitable in most cases. If one hole for securing a fragment aligns with a structurally unsound area on the opposite side, another hole may be used. If no holes are ideally situated, the surgeon may slightly rotate the nail to achieve a more favorable alignment. It is preferred that the nail accommodate three or four screws at the proximal end, with each of the proximal screw holes occupying a different plane.

The surgical implant procedure entails making an incision in the patient's shoulder above the humeral head to expose the head. An awl or reamer creates the aperture 80 at the anatomical neck 78, enabling the insertion of a broach having the same profile as the nail. The broach forms the bore 52 to a depth sufficient to receive the nail, but no deeper than necessary, thereby avoiding excessive disruption of tissue. The broach is then removed, and the nail is inserted. A drill guide jig is precisely registered with the notch 34, and includes drill guides that are thus aligned with the transverse holes. With the jig secured to the proximal end of the nail, a plurality of drill guides are registered with the holes in the implanted nail such that the drill bit may pass through the nail holes without contact. Through each guide hole, a hole is drilled through the bone on either side of the nail hole. An incision may be made to facilitate entry of the drill through soft tissues surrounding the bone. The drilled hole should be small enough to firmly engage the screw threads, but large enough to avoid splitting of the bone. A clearance hole of larger diameter may also be drilled through only the near side of the bone to avoid engaging the screw threads. Consequently, compression is achieved by the engaging threads on the far side and the screw head on the near side. For additional securement of fragments, cannulated screws may be used to permit wires to be passed through the screws and wrapped about any unsecured fragments.

The illustrated humeral nail is manufactured by providing a titanium or stainless steel rod, turning it to the desired taper, and leaving an excess portion at the shank with an registration slot for aligning subsequent manufacturing operations. The nail is bent to the desired arc, then drilled with all transverse holes. The registration portion is cut away, and the butt portion finished, resulting in the desired length. Finally, the nail is given a suitable surface finish.

Although this description refers to a particular embodiment, the following claims are not intended to be so limited.

We claim:

1. An elongated tapered nail for securing fractures of the proximal humerus comprising:

an elongated body having a curved shank configured to occupy an upper portion of the proximal humerat shaft, and a contiguous butt portion extending proximally from the shank and configured to occupy the humerat cortex;

the butt portion being shorter than the shank and defining a plurality of at least three transverse holes, each defining a hole axis, with the three hole axes angularly offset from each other, such that the holes may receive fasteners attached to fragments of the humeral cortex.

2. The nail of claim 1 wherein the curved shank includes a curved portion defining a curved central axis comprising an arc, and wherein the curved portion comprises at least half of the length of the shank.

3. The nail of claim 1 wherein the butt portion defines a central axis and each of the transverse holes is oriented on a respective hole axis, and wherein at least one of the hole axes is angularly offset from another of the hole axes by an acute angle.

4. The nail of claim 1 having a total length of less than 8 inches.

5. The nail of claim 1 defining a central axis having at least a curved portion, the axis occupying a reference plane.

6. The nail of claim 5 wherein at least one of the transverse holes in the butt portion is offset from the reference plane by an acute angle.

7. The nail of claim 5 wherein at least one of the transverse holes in the butt portion is offset from the reference plane by less than 45 degrees.

8. The nail of claim 5 wherein at least one of the transverse holes in the butt portion is offset from the reference plane by about 30 degrees.

9. The nail of claim 5 wherein the transverse holes in the butt portion include at least two holes angularly offset each by a respective angle from the perpendicular to the reference plane.

10. The nail of claim 1 wherein the elongated body defines a distal transverse hole and comprises a tip portion extending distally beyond the distal hole by at least one inch.

11. The nail of claim 1 wherein the elongated body defines a distal transverse hole and comprises a tip portion extending distally beyond the distal hole by a distance 20–50% of the total length of the nail.

12. The nail of claim 1 wherein the elongated body defines a distal transverse hole and comprises a tip portion extending distally beyond the distal hole, and wherein the tip portion is more tapered over at least a portion of its length than is the remainder if the body.

13. The nail of claim 1 having a profile that substantially passes within its own envelope.

14. The nail of claim 1 wherein the entire butt portion has a straight cylindrical profile.

15. The nail of claim 1 wherein each of the transverse holes occupies a different plane.

16. The nail of claim 1 wherein the transverse holes are closely grouped, the spacing along the length of the nail between the axes of adjacent holes being less than the lengths of the holes, such that the holes provide securement for portions of a humeral head when the nail is fully implanted in a humerus.

17. The nail of claim 1 wherein the butt portion terminates at a proximal end, and wherein the transverse holes are closely grouped near the proximal end with all of the transverse holes being closer to the butt end than to a midpoint of the entire nail, such that the holes provide securement for portions of a humeral head when the nail is fully implanted in a humerus.

18. The nail of claim 1 wherein the butt portion has a length of less than two times the diameter of the butt portion such that the holes are closely grouped.

19. A humeral nail for securing fragments of a fractured proximal humeral cortex to a humeral shaft, the nail comprising:

a curved tapered shank having a curved conical profile with a diameter that is a linear function of position along the shank, the shank having a proximal end having a first diameter, and a distal end having a smaller second diameter, with the shank having a substantially constant shaft taper angle therebetween, the shank defining at least a first securement hole;

a concavely tapered extending portion extending from the distal end of the shank, having a proximal end abutting the distal end of the shank at a transition;

the extending portion having the second diameter at its proximal end to provide a continuous surface at the transition;

the extending portion having a greater taper angle at its proximal end than the shaft taper angle, such that the transition between the shaft and the concavely tapered portion comprises a convex crest; and the extending portion having a taper angle that diminishes toward the distal end of the shank.

20. The nail of claim 19 wherein the taper angle at the distal end of the extending portion is zero.

21. The nail of claim 19 further comprising a cylindrical terminal portion extending from the distal end of the extending portion and having a distal end comprising a rounded nose.

22. The nail of claim 21 further comprising a cylindrical butt portion extending from the proximal end of the shank and defining a plurality of second securement holes and an alignment element, such that the position of the securement holes may be determined by the position of the alignment element.

* * * * *

UNITED STATES PATENT AND TRADEMARK OFFICE
CERTIFICATE OF CORRECTION

PATENT NO.    : 5,472,444
DATED         : December 5, 1995
INVENTOR(S)   : Randall J. Huebner and Gene L. Conrad It is certified that error appears in the above-identified patent and that said Letters Patent is hereby corrected as shown below:

Column 5,
Lines 47 and 49, delete "humerat" and insert -- humeral -- therefor.

Column 6,
Line 25, delete "if" and insert -- of -- therefor.

Signed and Sealed this

Twenty-ninth Day of June, 2004

JON W. DUDAS
*Acting Director of the United States Patent and Trademark Office*

(12) EX PARTE REEXAMINATION CERTIFICATE (6086th)
United States Patent
Huebner et al.

(10) Number: US 5,472,444 C1
(45) Certificate Issued: Jan. 8, 2008

(54) HUMERAL NAIL FOR FIXATION OF PROXIMAL HUMERAL FRACTURES

(75) Inventors: Randall J. Huebner, Aloha, OR (US); Gene L. Conrad, Aloha, OR (US)

(73) Assignee: Acumed LLC, Hillsboro, OR (US)

Reexamination Request:
No. 90/007,923, Feb. 10, 2006

Reexamination Certificate for:
Patent No.: 5,472,444
Issued: Dec. 5, 1995
Appl. No.: 08/242,738
Filed: May 13, 1994

Certificate of Correction issued Jun. 29, 2004.

(51) Int. Cl.
*A61B 17/68* (2006.01)
*A61B 17/72* (2006.01)

(52) U.S. Cl. .............................. 606/64; 606/62
(58) Field of Classification Search .................. None
See application file for complete search history.

(56) References Cited

U.S. PATENT DOCUMENTS

| | | |
|---|---|---|
| 4,622,959 A | 11/1986 | Marcus |
| 5,034,013 A | 7/1991 | Kyle |
| 5,248,313 A | 9/1993 | Greene |
| 5,441,500 A | 8/1995 | Seidel |

FOREIGN PATENT DOCUMENTS

EP 0355 411 2/1990

OTHER PUBLICATIONS

ALTA Modular Trauma System, 1992 (Ex. 1).
Timothy J. Bray (Editor), Techniques on Fracture Fixation as Practiced by the Reno Orthopaedic Clinic (Ex 2).
The Chandler Tibial Nail, 1990 (Ex. 5).
Uniflex Humeral Nail System, 1991 (two copies) (Ex. 8).
AIM Titanium Tibial Nail–Surgical Technique (Ex. 9).
J. Bone Joint Surg. 1994; 76–B; Supp II & III, Australian Orthopaedic Association, Sep. 24–28, 1993, A.M. Ingman, A New Locked Nail for Proximal Humeral Fractures, p. 119 (Ex. 11).
Declaration of Michael W. Chapman, M.D. (Ex. 12).
Jon C. Thompson, M.D., Netter's Concise Atlas of Orthopaedic Anatomy, 2002 (Ex. 13).
Scott Hal Kozin, M.D. and Anthony Clayton Berlet, M.D., Handbook of Common Orthopaedic Fractures, 2000 (Ex. 14).
Plaintiffs' First Supplemental Response to Defendant's First Set of Interrogatories, Mar. 2, 2005 (Ex. 15).

*Primary Examiner*—David O. Reip

(57) ABSTRACT

An elongated tapered nail or rod having an elongated body with a curved tapered shank that may be secured within a proximal portion of the humeral shaft, with a contiguous butt portion of the nail extending proximally from the shank to provide a solid foundation to which the humeral head fragments may be secured. The butt portion has transverse holes oriented at selected angles to receive fasteners attached to the fragments. The nail has a varying taper angle that creates a ridge positioned away from the distal tip, reducing stress concentrations on the bone that may occur at the tip of any reinforcing implant.

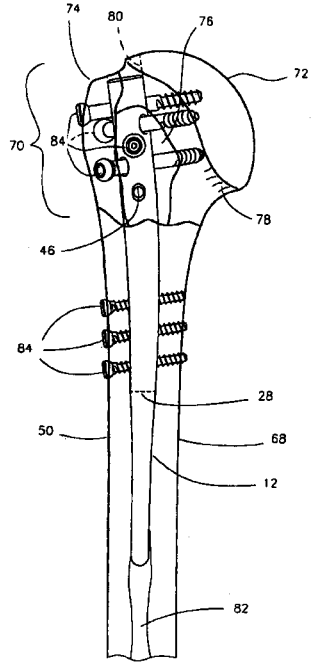

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–22 is confirmed.

* * * * *